United States Patent
Collins et al.

(10) Patent No.: US 9,119,559 B2
(45) Date of Patent: Sep. 1, 2015

(54) METHOD AND SYSTEM OF GENERATING A 3D VISUALIZATION FROM 2D IMAGES

(75) Inventors: Jeffrey B. Collins, Caledon (CA); Frederic Lachmann, Toronto (CA); Ted Timar, Toronto (CA); Desmond Ryan Chung, Thornhill (CA); Janet R. Sterritt, Hollis, NH (US); Scott Reginald Norris, Kitchener (CA); Erin M. Walsh, Oakville (CA); Tatiana Sheinfeld, Toronto (CA); Sumit Nath, Toronto (CA); Ning Hu, Markham (CA)

(73) Assignee: Salient Imaging, Inc., Hollis, NH (US)

( * ) Notice: Subject to any disclaimer, the term of this patent is extended or adjusted under 35 U.S.C. 154(b) by 162 days.

(21) Appl. No.: 13/524,194

(22) Filed: Jun. 15, 2012

(65) Prior Publication Data

US 2013/0016092 A1 Jan. 17, 2013

Related U.S. Application Data

(60) Provisional application No. 61/497,656, filed on Jun. 16, 2011.

(51) Int. Cl.
*G06T 15/00* (2011.01)
*G06T 17/00* (2006.01)
*A61B 8/08* (2006.01)
*A61B 8/00* (2006.01)
*G06T 19/00* (2011.01)
*G06T 7/60* (2006.01)

(52) U.S. Cl.
CPC .............. *A61B 8/0891* (2013.01); *A61B 8/466* (2013.01); *A61B 8/469* (2013.01); *A61B 8/5215* (2013.01); *A61B 8/5269* (2013.01); *G06T 7/606* (2013.01); *G06T 19/003* (2013.01); *A61B 8/483* (2013.01); *A61B 8/488* (2013.01); *G06T 2207/10132* (2013.01); *G06T 2207/30101* (2013.01); *G06T 2207/30172* (2013.01); *G06T 2210/41* (2013.01); *G06T 2219/028* (2013.01)

(58) Field of Classification Search
CPC combination set(s) only.
See application file for complete search history.

(56) References Cited

U.S. PATENT DOCUMENTS

| | | | |
|---|---|---|---|
| 2008/0278487 A1* | 11/2008 | Gobert | 345/420 |
| 2010/0158332 A1 | 6/2010 | Rico et al. | |
| 2010/0171740 A1* | 7/2010 | Andersen et al. | 345/424 |
| 2011/0299750 A1* | 12/2011 | Cool et al. | 382/131 |
| 2012/0321153 A1* | 12/2012 | Dwivedi et al. | 382/128 |

OTHER PUBLICATIONS

C.H. Li and C.K. Lee, "Minimum Cross Entropy Thresholding", Pattern Recognition, vol. 26, p. 617-625 (1993).
M. Luessi, M. Eichmann, G.M. Schuster and A. Katsaggelos, "Framework for Efficient Optimal Multilevel Image Thresholding", Journal of Electronic Imaging, v. 18, No. 1, Jan.-Mar. 2009, p. 013004-1-013004-10.

(Continued)

*Primary Examiner* — Leon T Cain, II
(74) *Attorney, Agent, or Firm* — Hayes Soloway PC

(57) ABSTRACT

The invention relates to the field of computerized generation of a visualization from a plurality of images. In particular, the invention relates to generating a three-dimensional (3D) visualization from a plurality of two-dimensional (2D) medical images. The images may be obtained from an ultrasound device. Regions of interest are segmented in at least two images and the region of interest is then tracked and segmented among the remaining images.

19 Claims, 16 Drawing Sheets

(56) References Cited

OTHER PUBLICATIONS

A. Fitzgibbon, M. Pilu and R.B. Fisher, "Direct Least Square Fitting of Ellipses", IEEE Trans. PAMI, v. 21, No. 5, May 1999, p. 476-480.
Guerrero, J.; Salcudean, S.E.; McEwen, J.A; Masri, B.A.; Nicolaou, S, Real-Time Vessel segmentation and Tracking from Ultrasound Imaging Applications; Medical Imaging, IEEE Transactions on, Aug. 2007, vol. 26, Issue 8, 1079-1090.
B.K. Lai, et al., Pixel Distribution Analysis of B-Mode Ultrasound Scan Images Predicts Histologic Features of Atherosclerotic Carotid Plaques, J. Vasc. Surg. vol. 35, pp. 1210-1217, 2002.
E.W. Dijkstra, "A Note on Two Problems in Connexion with Graphs", Numerische Mathematik, v. 1, 1959, p. 269-271.
R. Nock and F. Nielsen, "Statistical Region Merging", IEEE Trans. PAMI, v. 26, No. 11, Nov. 2004, p. 1452-1458.
F. Calderero and F. Marques, "Region Merging Techniques using Information Theory Statistical Measures", IEEE Trans. Image Processing, v. 19, No. 6, Jun. 2010, p. 1567-1586.
P. Felzenszwalb and D. Huttenlocher, "Efficient Graph-Based Image Segmentation", Int. J. Comp. Vision, v. 59, No. 2, Sep. 2004.
P.L. Rosin, "Shape Partitioning by Convexity", IEEE Trans. Systems, Man and Cybernetics, Part A: Systems and Humans, v. 30, No. 2, Feb. 2000, p. 202-210.

* cited by examiner

METHOD AND SYSTEM OF GENERATING A 3D VISUALIZATION FROM 2D IMAGES

CROSS REFERENCE

The present application claims priority from U.S. Patent Application No. 61/497,656, filed Jun. 16, 2011, the contents of which are incorporated by reference herein.

FIELD OF INVENTION

The invention relates generally to the field of computerized generation of a visualization from a plurality of images. In particular, the invention relates to generating a three-dimensional (3D) visualization from a plurality of two-dimensional (2D) medical images.

BACKGROUND OF INVENTION

Vascular diseases, caused by a gradual accumulation of plaque on the walls of blood vessels, are among the leading causes of death in North America and around the globe. The diseases consist of carotid artery narrowing that can lead to embolism, a dislodgement of plaque fragments, which travel to the brain causing strokes.

Sonography is an ultrasound-based imaging technique and is generally used for imaging soft tissues of the body. Typically, a transducer is used to scan the body of a patient. An ultrasound image of body tissues, blood vessels and organs is produced from ultrasound echoes received by the transducer. Feature descriptors of shape, contour, margin of imaged masses, echogenicity and velocity are generally used in diagnosis of medical ultrasound images. Sonography has been shown to be an effective blood vessel imaging modality.

Ultrasound provides a non-invasive means for visualizing various tissues within the human body and it has been successfully used as an early detection and diagnosis of the accumulation of plaque in blood vessels. By detecting the exact location, shape and morphology of the plaque, the ultrasound imaging modality not only improves the patient's prognosis, but also lowers the overall cost of their treatment. However, the ultrasound images tend to be filled with speckle noise and other artifacts, due to the sporadic nature of high frequency sound waves.

By analyzing the ultrasound images, a professional is able to estimate the accumulation of plaque at various locations in the blood vessel. However, this requires manually comparing several ultrasound images and determining whether narrowing of a blood vessel as shown in an image is due to plaque, another cause, or measurement error.

It is an object of the present invention to mitigate or obviate at least one of the above mentioned challenges.

SUMMARY OF INVENTION

In one aspect, a system for generating a three dimensional visualization from a plurality of two dimensional images obtained by a transverse scan is provided, the system comprising: (a) a segmentation utility to segment and track a region of interest in each image; and (b) a visualization utility to render a three-dimensional visualization using said segmented and tracked region of interest.

In another aspect, a method for generating a three dimensional visualization from a plurality of two dimensional images obtained by a transverse scan is provided, the method comprising: (a) segmenting and tracking, by a processor, a region of interest in each image; and (b) rendering a three-dimensional visualization using said segmented and tracked region of interest.

BRIEF DESCRIPTION OF DRAWINGS

Embodiments will now be described by way of example only with reference to the appended drawings wherein.

DETAILED DESCRIPTION OF EMBODIMENTS

Figure 1:
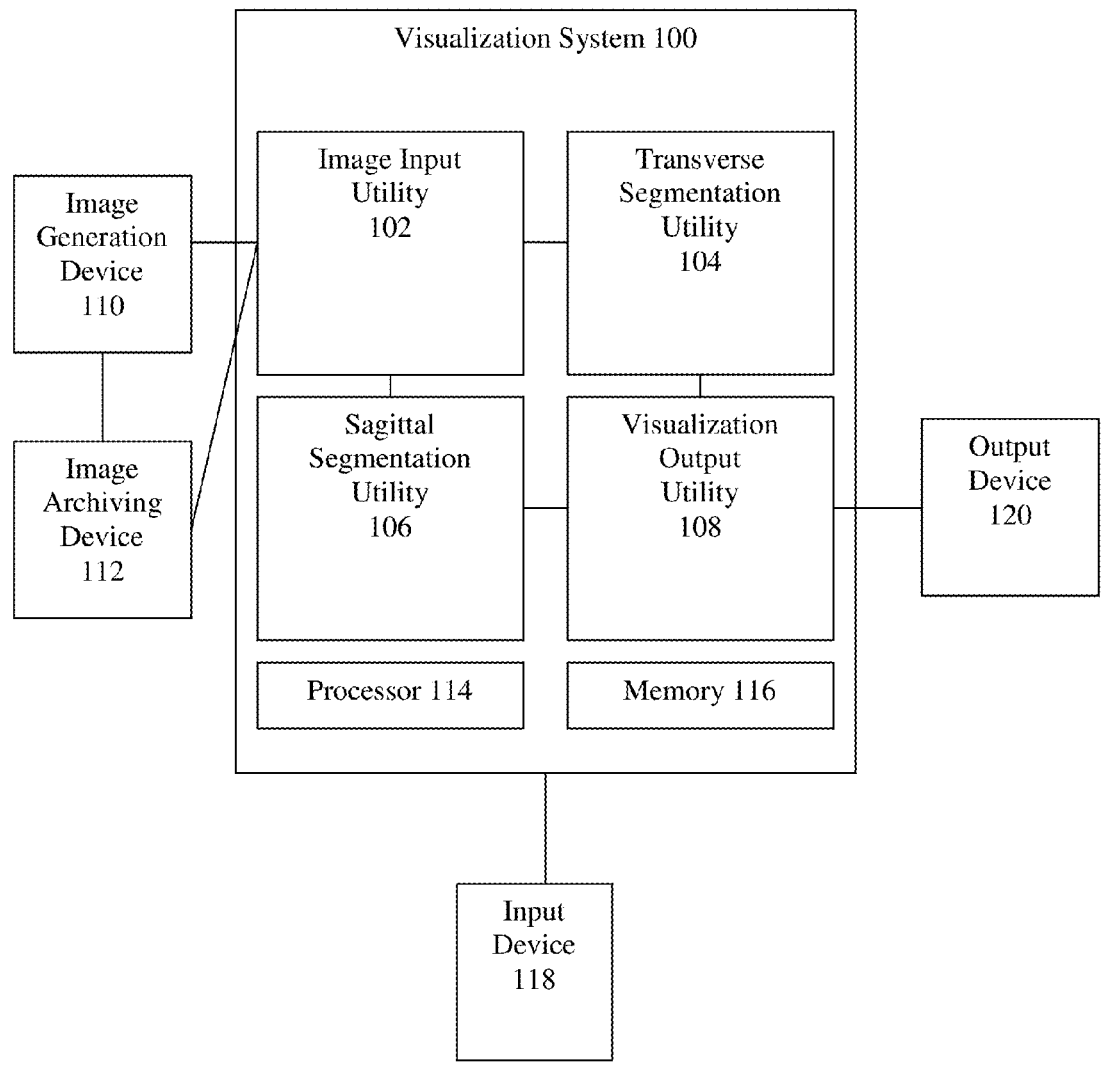
FIG. 1 is a schematic diagram of a visualization system.

Embodiments will now be described with reference to the figures. It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It will also be appreciated that any module, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Any application or module herein described may be implemented using computer readable/executable instructions that may be stored or otherwise held by such computer readable media.

The present invention relates to the field of computerized generation of visualizations from a plurality of images. The present invention provides a system, method and computer program for generating a three-dimensional (3D) visualization from a plurality of two-dimensional (2D) medical images. Initially, a plurality of 2D images are obtained. A region of interest in one or more of the images is selected. The region of interest is segmented in the one or more images in which it is selected. The region of interest is then tracked and segmented in each other image. Alternatively, or in addition, segmentation may be performed on a plurality of areas within the region of interest. Measurements may be made of the region of interest. A 3D visualization of the region of interest is then generated.

The present invention can be applied to 3D visualization of any entity, including, for example, blood vessels to observe plaque accumulation, other organs including skin to observe lesions, or inanimate objects.

Referring to FIG. 1, in one aspect, a visualization system 100 is provided. The visualization system comprises an image input utility 102, transverse segmentation utility 104, sagittal segmentation utility 106, and visualization output utility 108. The image input utility 102 is operable to obtain a plurality of input images from an image generation device 110. The image generation device 110 may be communicatively coupled to the image input utility 102, or the image generation device 110 may be communicatively coupled to an image archiving device 112 that is further communicatively coupled to the image input utility 102.

The image generation device 110 may, for example, be a medical image acquisition system, such as an ultrasound imaging system, from which ultrasound images are acquired in real-time from a patient. An ultrasound device generally comprises an ultrasound transducer and is operable to generate a transverse scan and may be further operable to generate a sagittal scan.

The image archiving device 112 may be an image archive, such as a Digital Imaging and Communications in Medicine (DICOM)-compliant archive, which stores on a computer readable storage medium one or more media images acquired by imaging systems. The image archiving device 112 may also be image data already retrieved by a physician and stored on a storage medium local to a computer system that implements the visualization system 100.

The image input utility 102 may further extract acquisition parameters stored in or transmitted together with medical image data. The image input utility 102 processes DICOM data and extracts these parameters from DICOM data headers in the image data. It may also be implemented to handle non-standard data format and extract those parameters from image data stored in any proprietary format. Acquisition parameters include hardware parameters, such as those due to variations between ultrasound transducer equipment of different vendors, which include depth and transducer frequency, and those operator parameters, such as technologists' equipment or acquisitions settings, examples of which include transducer pressure and time-gain compensation. These hardware and operator parameters can be extracted from data headers as defined in the DICOM standard or transmitted directly with image data when images acquired by imaging systems are processed in real-time.

The visualization output utility 108 is operable to generate a display signal enabling a visualization to be graphically output to an operator of the visualization system 100. For example, the visualization output utility 108 may be connected to an output device 120, such as a computer monitor or touch-screen display.

The visualization system 100 may comprise a processor 114 and a memory 116. The memory 116 has stored thereon computer instructions which, when executed by the processor 114, provide the functionality of the image input utility 102, transverse segmentation utility 104, sagittal segmentation utility 106 and visualization output utility 108. It will be appreciated that the visualization system may alternatively be embodied in a distributed computing environment comprising a plurality of processors and memories.

The visualization system 100 may further comprise an input device 118 operable to receive input from an operator. The input device 118 may comprise a keyboard, keypad, control switch, mouse, touch-screen display, stylus, another input device or any combination thereof.

Figure 2:
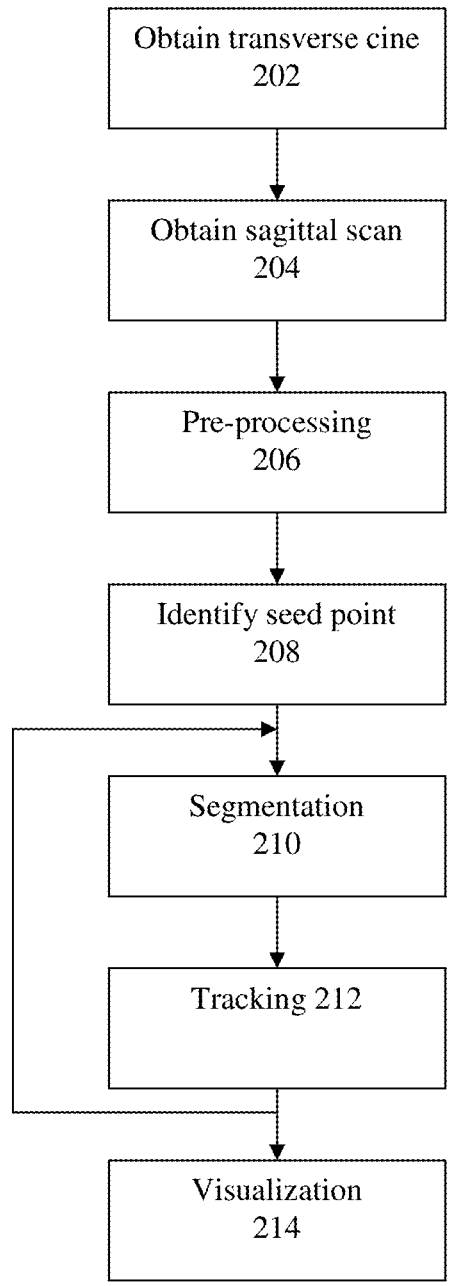
FIG. 2 is a flowchart describing a visualization method.

Referring now to FIG. 2, in another aspect a visualization method 200 may comprise a sequence of image processing routines and visualization generating routines applied to a plurality of input images. The input images may be obtained 202, 204 from the image generation device. The image generation device may, for example, be the ultrasound device. An operator of the ultrasound transducer of the ultrasound device may obtain an ultrasound cine using a freehand sweep of a target area that includes the region of interest. For example, a freehand ultrasound scan of the carotid artery may be performed to obtain an ultrasound cine. An operator may, for example, measure for a particular patient the distance between two landmarks, for example from the patient's clavicle to mid-mandible. These measurements may be provided as input to the image processing routines and visualizing routines.

The operator may configure the ultrasound transducer to obtain a transverse cine 202 at a particular scan depth. The operator may perform a freehand scan by operating the ultrasound transducer to acquire the transverse cine using a single slow and steady sweep of the target area. The ultrasound transducer obtains a plurality of images corresponding to the frames of the transverse cine. The ultrasound device is operable to provide the transverse cine to the image input utility either directly or via an image archiving device. In the event that the cine is provided to the image archiving device, which may be a DICOM archive, the input device may be operable to perform several image processing tasks on the obtained images prior to storage on the DICOM archive. For example, one of these image processing tasks may be a DICOM cropping step.

In one image obtaining example, for a carotid artery scan, the transverse cine preferably is obtained from the proximal end of the common carotid artery (CCA) to the distal end of the internal carotid artery (ICA) at an angle of entry to provide the best possible view of any carotid plaque, which is generally the posterior angle. The target area is optimally obtained near the mid-point of the sweep. Preferably, the angle and depth at which the cine is obtained is substantially constant throughout the sweep.

Figure 3:
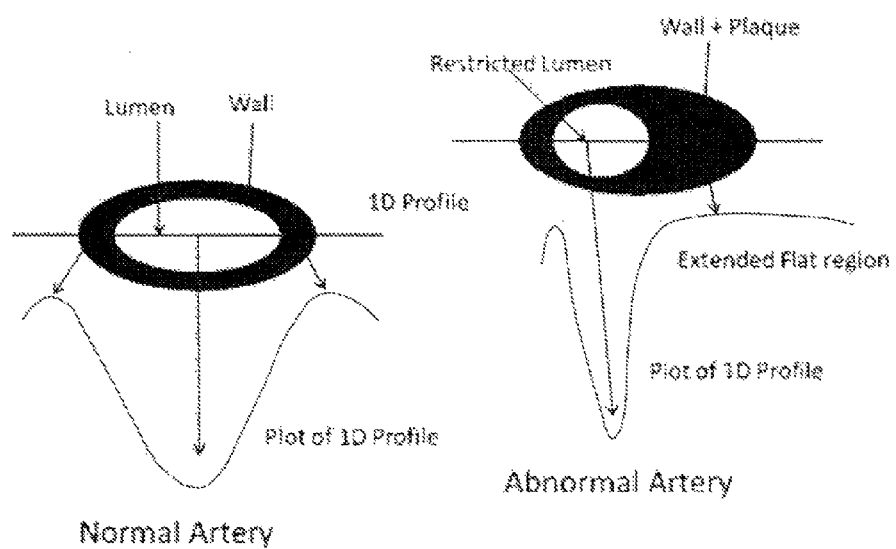
FIG. 3 is a graphical representation of a normal and abnormal artery.

Particular ultrasound device configurations may result in more desirable results. For example, the time gain control of the ultrasound device may be configured to present uniform gain across the transverse cine, top to bottom. It will be appreciated that the operator may wish to fine tune the configuration of the ultrasound device on a patient-by-patient basis to distribute the dynamic range of intensities as widely as possible over the target area. For example, at an overall image gain around 50%, blood in a carotid artery may be seen as black while visibly distinct artery walls (adventitia) may be seen as nearly white but still distinct from any calcified tissue. A full white intensity is preferably reserved for calcified tissue. The luminal region is preferably the darkest among all neighbouring regions, e.g., having greatest grayscale intensity. Therefore, any particular scan can be represented by a Gaussian model as shown in FIG. 3. Using this model, segmentation of the ICA or CCA luminal regions can be expressed as isolation of the longest continuous 3D-region between two marked images.

The operator may additionally obtain a sagittal scan 204 to provide a color sagittal scan that, for a carotid artery scan, includes the bifurcation of the CCA and the plaque. The resulting distance observable between the bifurcation and the start or end of the plaque can be used as input to the visualization output utility 108.

Furthermore, the operator may obtain the transverse and sagittal scans either unilaterally, being either the left or right carotid artery, for example, or bilaterally, being both carotid arteries, for example.

The visualization method 200 may include pre-processing 206 of the plurality of cine frames by the transverse segmentation utility. Pre-processing may comprise a de-noising, i.e., noise-removal or noise-reduction, to remove or reduce noise from each input image. Noise can be removed or reduced, for example, by applying to an input image an edge preserving diffusion process. Such a process can be used to remove or reduce noise from the image while maintaining and, preferably, enhancing edges of objects in the image. Pre-processing may further comprise noise reduction and/or normalization. Many different de-noising and normalization processes may be used. Some such processes are described in U.S. patent application Ser. No. 12/643,337, which is incorporated herein by reference.

The visualization method 200 further comprises identifying a seed point 208 that can be used to determine the region of interest. The visualization method 200 further comprises segmentation 210. Segmentation enables accurate detection of plaque inside blood vessels including by measuring the lumen diameter and area measurements that enable the operator to more accurately identify plaque accumulation. For example, a smaller lumen diameter would indicate increased plaque accumulation. The transverse segmentation utility operates on each of the plurality of images in the ultrasound cine. The visualization method 200 further comprises tracking and segmenting 212 the region of interest among the images. Finally, the visualization output utility generates a visualization of the region of interest in three dimensions 214.

Figure 4:
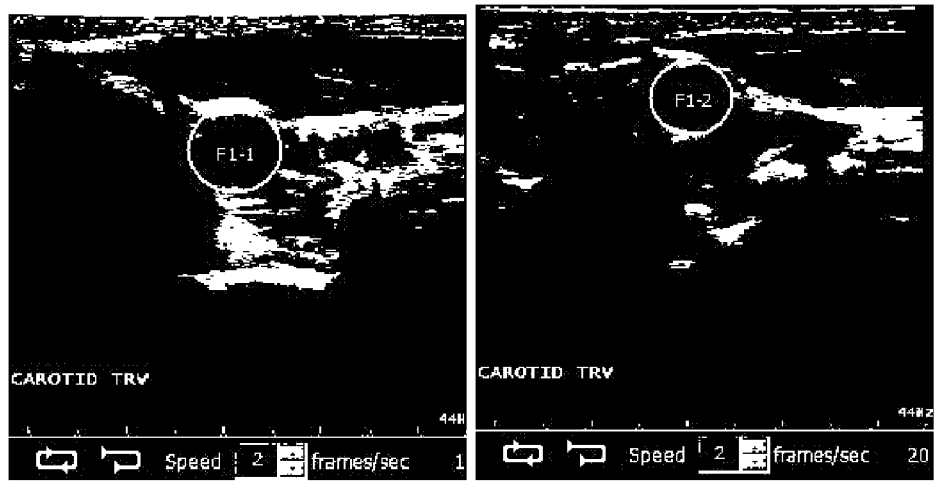
FIG. 4 is a graphical representation of two images having a region of interest.

Referring now to FIG. 4, two frames in a cine are shown. The region of interest is preferably provided on at least two of the input images. For example, the input images may comprise the first and last frames of the cine, two intermediate frames in the cine, or any other combination of frames in the cine. If the region of interest is identified on two intermediate frames in the cine, the transverse segmentation utility may define the intermediate frames as the first and last frame to process in accordance with the steps described below. Alternatively, the frames prior to the first frame and/or after the second frame for which the region is identified can also be processed by extrapolating the region of interest that is found from those frames between the first frame and the second frame by the transverse segmentation utility. A similar approach can be used where the first frame of the cine and an intermediate frame are used, or where an intermediate frame of the cine and the last frame are used.

Figure 5:
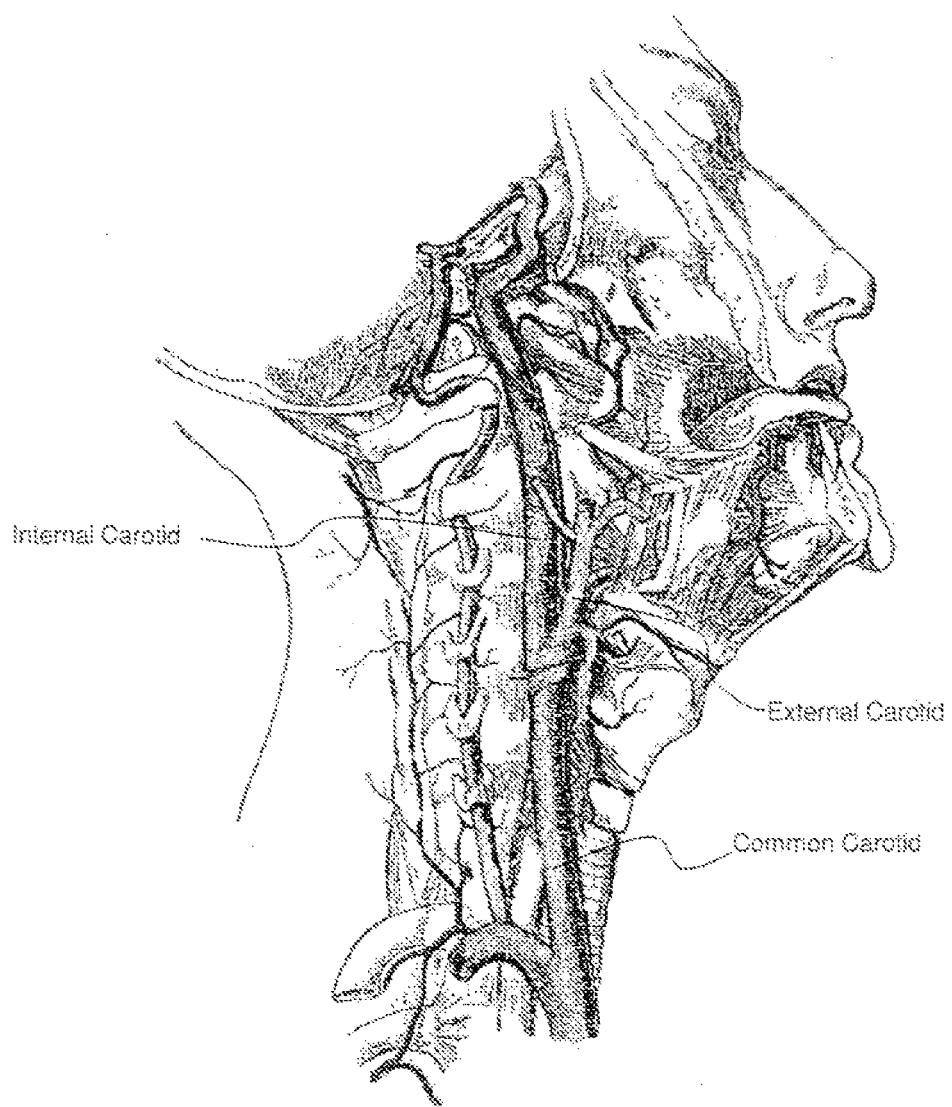
FIG. 5 is a graphical representation of the human body in the area of the carotid artery.

FIG. 5 shows a preferred example wherein one region of interest is provided in the distal CCA region and another in the proximal ICA region. Each image may comprise or be associated with a label, which enables the operator to indicate the portion along the ICA or CCA that the image is associated. For example, the operator may label a distal CCA image with a distal CCA label.

Preferably, the operator is directed not to mark a region of interest in the bifurcation area, since the shape of the artery differs in that area relative to the ICA and CCA regions. Preferably, for the CCA segment, the last image should be located before the bifurcation, while the start image for of the ICA should begin after resolving the ECA.

To identify the regions of interest, the visualization system enables an operator to manually provide an outline of each region of interest using the input device. Alternatively, the visualization system may enable an operator to provide one or more seed points based on which an outline can be approximated by segmentation. The transverse segmentation utility may also be provided with one or more preconfigured region of interest parameters to enable the transverse segmentation utility to accurately identify the region of interest. For example, the region of interest parameters may include a radius value that enables the transverse segmentation utility to initiate segmentation based on the region of interest being a circle having a center corresponding to the seed point and an outline based on the radius value; or a ellipse formula for defining an ellipse surrounding one or more seed points; or by using a preconfigured approximate size of the region of interest. The radius should preferably be selected to enclose the region of interest but not overlap, or minimally overlap, neighbouring regions, such as the jugular vein, for example.

The transverse segmentation utility may further identify more than one region of interest by segmentation of the image 202.

Figure 6:
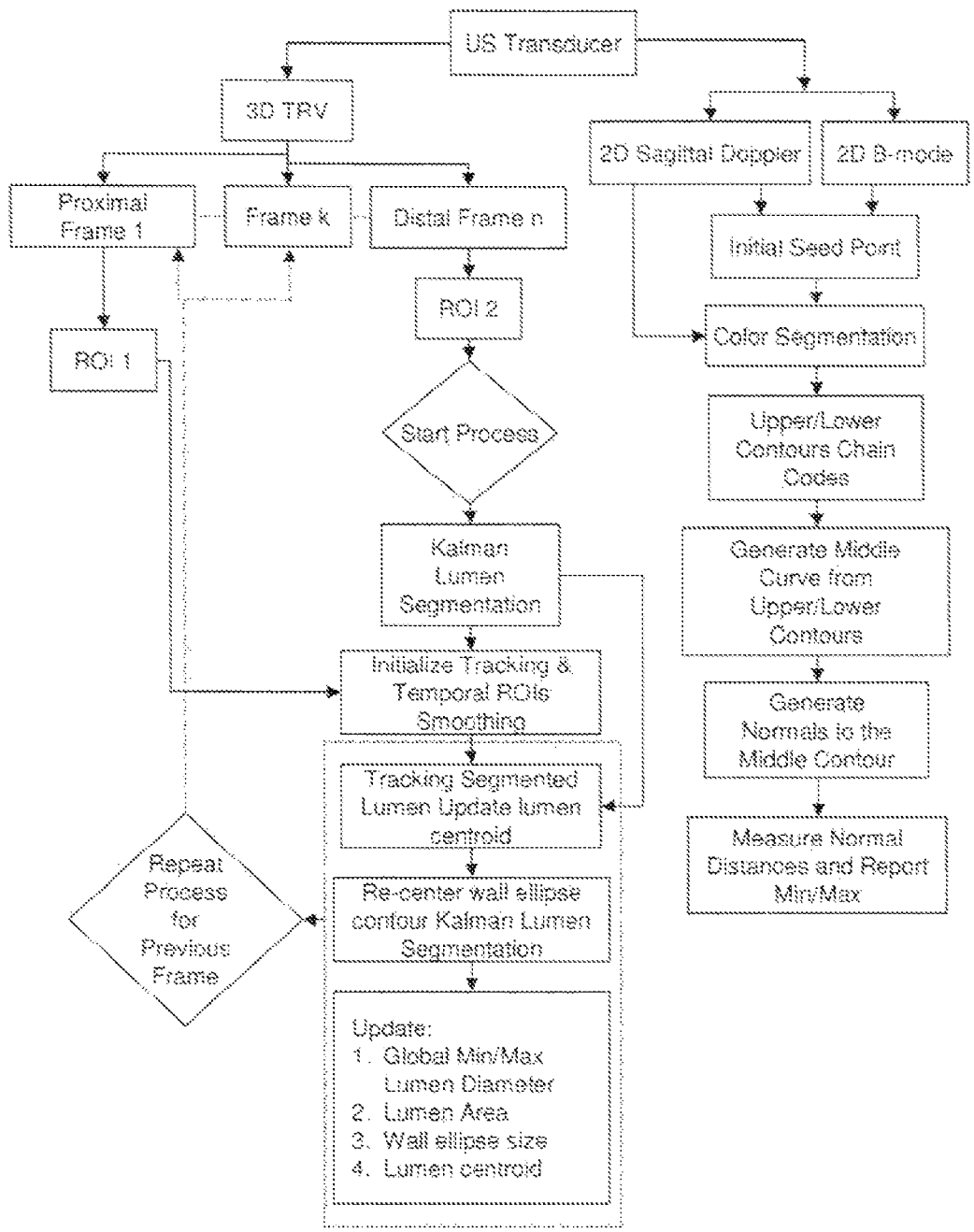
FIG. 6 is a flowchart describing segmentation.

Referring now to FIG. 6, the transverse segmentation utility may provide initial segmentation, segmentation and contour refinement. Initial segmentation comprises segmentation of the region of interest in a first, manually or partly manually marked image. Segmentation comprises segmentation of the region of interest in the remaining images. Contour refinement comprises refinement of the output of segmentation given the results of segmentation from other images in the plurality of images.

Various segmentation methods may be used, including the segmentation process described in U.S. patent application Ser. No. 12/643,337, incorporated herein by reference. Segmentation may further comprise a machine learning based segmentation process.

The lumen segmentation process may be based on a Kalman filtering approach and comprise projecting from the lumen centroid a plurality of radial profiles at angularly equi-spaced radii. The radial profiles may be projected to an edge of the lumen, which may be observed, for example, by a color or shade change that are determined to correspond to the lumen edge. The end-points of the radial profiles, when joined, can be considered to form a closed contour that provides the segmentation result. This segmentation result may further be refined. The resulting contour often resembles an ellipse.

Initial segmentation follows. Having enabled the operator to select the location of the operator-defined regions of interest, the transverse segmentation utility may apply an image analysis process to stabilize the regions of interest to increase consistency and thereafter may segment from the image the lumen and outer wall. A similar approach may be used to generate the contour of the intima and adventitia.

A grid pattern may be generated, for example a 5×5 grid, surrounding the center point of the operator-defined region of interest, and the results averaged, as is now described. The region of interest may be cropped and a multi-level thresholding algorithm (such as that described in C. H. Li and C. K. Lee, "Minimum Cross Entropy Thresholding", Pattern Recognition, vol. 26, p. 617-625 (1993), and M. Luessi, M. Eichmann, G. M. Schuster and A. Katsaggelos, "Framework for Efficient Optimal Multilevel Image Thresholding", Journal of Electronic Imaging, v. 18, no. 1, January-March 2009, p. 013004-1-013004-10, both incorporated herein by reference) may be applied to approximately isolate the luminal region. As previously mentioned, the lumen may be modeled as having the smallest grayscale intensity in the image. By applying k-levels of thresholding, all pixels within the first threshold level may be determined to fall within the region of interest. A connected-component filtering process may be applied to disambiguate "Siamese-twin" cases (i.e., Jugular vein lying in the close vicinity of the carotid artery). The central object output by the filtering process may be selected.

Having obtained the region of interest, an algorithm (such as that described in A. Fitzgibbon, M. Pilu and R. B. Fisher, "Direct Least Square Fitting of Ellipses", IEEE Trans. PAMI, v. 21, no. 5, May 1999, p. 476-480, incorporated herein by reference) may be applied to obtain a best-fitting ellipse to completely encapsulate the region of interest. The foregoing connected-component filtering process enables a reduction in distortion of ellipse parameters in case confounding objects have not been removed from the vicinity of the object. Ellipse parameters may be computed at each grid-point and an average may be obtained. The best-fitting ellipse obtained from this step may be balanced with the operator-defined region of interest by a heuristic that suitably scales the two results and blends them to provide a region of interest.

Next, the transverse segmentation utility may perform temporal smoothing on the images or the regions of interest within the images. In particular cines, the distance between frames results in relatively large variations in the segmented lumen size from frame to frame. The segmentation algorithm may temporally smooth the regions of interest 204 in each frame based on the region of interest in frames that are manually or partly manually identified, in order to provide a smooth transition between the lumen size in the manually or partly manually identified frames and the lumen size in the other frames. The size of the outer wall may be weighted and smoothed out according to the size of the manually marked regions of interest. The weighting may be made at "k" frames before (or after) the manually marked frame. The value of "k" may be preconfigured to a number that is lower than the total number of frames, while maintaining low computation cost. For example, k may be preconfigured to 5. The weights may be computed from a z-shape fuzzy membership function and increase as the current frame approaches the marked frame.

Given the region of interest in the first cine frame, the transverse segmentation utility implements a tracking process to follow the anatomical structure of the blood vessel from one cine frame to the next. For example, the transverse segmentation utility may compute the best spatial location of the lumen's centroid for the current cine frame given the result of computing the best spatial location of the lumen's centroid for the previous cine frame. This may be performed using a cross-correlation process. For example, the maximum cross-correlation value of the previously segmented lumen image on the current frame may be used to derive the optimal lumen centroid. For example, the maximum cross-correlation may indicate the optimal lumen centroid, while other factors may also be considered. Such factors comprise the existence of nearby manually identified regions or interest ellipses and a weighted history of previously segmented lumen images. The optimal lumen centroid may further be used as input to the lumen segmentation process. The result of the tracking process applied to all frames is an optimized lumen centroid for each respective frame.

Preferably, a larger number of frames are provided so that the optimal lumen centroid from one frame differs minimally to that of the next frame, providing a more smooth and accurate visualization.

Given the optimal lumen centroids, the transverse segmentation utility is operable to re-center the segmented lumen for each image using the lumen segmentation process. The lumen segmentation process may be based on Kalman filtering and include known attributes regarding the shape and geometry of the blood vessel.

The wall sizes determined previously may then be updated based on the current segmented lumen and temporal region of interest size weighting. The largest region of interest size among all frames may be used as the wall size. The centroid of the profiles consists of the updated centroid coordinates for the particular image as determined by the tracking process. The lumen segmentation process predicts and corrects the spatial location of the lumen edge coordinates in the subsequent frame by using a non-linear state ellipse radius equation in the standard framework of the extended Kalman filters. The Kalman filter framework continuously maintains and updates its state information according to a stream of new, input. The Kalman filter state information represents the ellipse major and minor axis lengths and ellipse orientation angle, which assume the initial values supplied by the manually Marked regions of interest, or the previous frame's propagated estimates. The lumen edge coordinates for the current frame are then used in sequence to update the state information. In one example, the Kalman filters described in "Real-Time Vessel segmentation and Tracking from Ultrasound Imaging Applications", Guerrero, J.; Salcudean, S. E.; McEwen, J. A; Masri, B. A.; Nicolaou, S; Medical Imaging, IEEE Transactions on, August 2007, Volume 26, Issue 8, 1079-1090, incorporated herein by reference, may be applied.

The shape and geometry of the outer wall may be assumed to be elliptical, which in many cases accurately describes compressed veins. Furthermore, initiating the lumen segmentation process with known attributes of the elliptical shape approximation of the blood vessel does not constrain the lumen segmentation. The outer wall elliptical shape may be used to provide an initial search bracket for a lumen's edge detection process, rather than to parameterize the edge. The outer wall of the blood vessel can be estimated by the transverse segmentation utility using a preconfigured parameter related to the lumen centroid. In other words, the transverse segmentation utility may not need to perform segmentation to determine the size and centroid of the outer wall. For example, since the outer wall is generally an ellipse, the parameters of the outer wall ellipse may be dynamically generated for each new frame from the segmented lumen data using a preconfigured outer wall size factor. An outer wall size factor of 1.2, for example, may be used to guarantee that the generated outer wall includes the segmented lumen. The outer wall size factor can be applied by multiplying it with the lumen ellipse. The transverse segmentation utility may center the outer wall ellipse using the lumen centroid generated by the tracking process and the previously determined outer wall ellipse (i.e., short/long axis and ellipse orientation angle). Thus, the lumen segmentation process can generate the contour of the outer wall. The outer wall may be re-centered after operation of the tracking process, described below.

The temporal weighting may be achieved by filtering each transverse image, for example with a [5×5] median filter, to reduce noise in the image. A histogram of the median filtered image may be generated. Alternatively, the histogram can be generated by the imaging device concurrently with, for example, the DICOM cropping step.

Next, the outer wall ellipse mask is generated using the previously computed outer wall ellipse and updated lumen centroid. A k-means cluster data is generated, as is described in "Pixel Distribution Analysis of B-Mode Ultrasound Scan Images Predicts Histologic Features of Atherosclerotic Carotid Plaques", B. K. Lai, et al., J. Vasc. Surg. vol 35, pp 1210-1217, 2002, incorporated herein by reference. Finally, a plaque threshold value is generated based on the k-means cluster data.

The plaque threshold value can alternatively be generated at different depth values from the ultrasound image. This assumes a normal distribution, and the threshold value may be computed as specific quantile value.

Next, the radial profiles for the images can be generated from the centroid inside the outer wall mask.

Kalman filtering is then applied to the frame. A three-stage Kalman filtering process includes prediction, observation and reconciliation. This Kalman filtering process is described in "Real-Time Vessel segmentation and Tracking from Ultrasound Imaging Applications", Guerrero, J.; Salcudean, S. E.; McEwen, J. A; Masri, B. A.; Nicolaou, S; Medical Imaging, IEEE Transactions on, August 2007, Volume 26, Issue 8, 1079-1090, incorporated herein by reference. The resulting lumen centroids will be constrained inside the resulting outer wall. If not, any outliers can be removed from consideration.

Optionally, segmentation can be performed on a cropped portion of the images that is estimated or known to contain the region of interest, based on knowledge of the previously segmented lumen.

Finally, the plaque accumulation can be generated as the space between the lumen and the outer wall. The lumen and the outer wall coordinates for each image are then stored to the memory.

Figure 7:
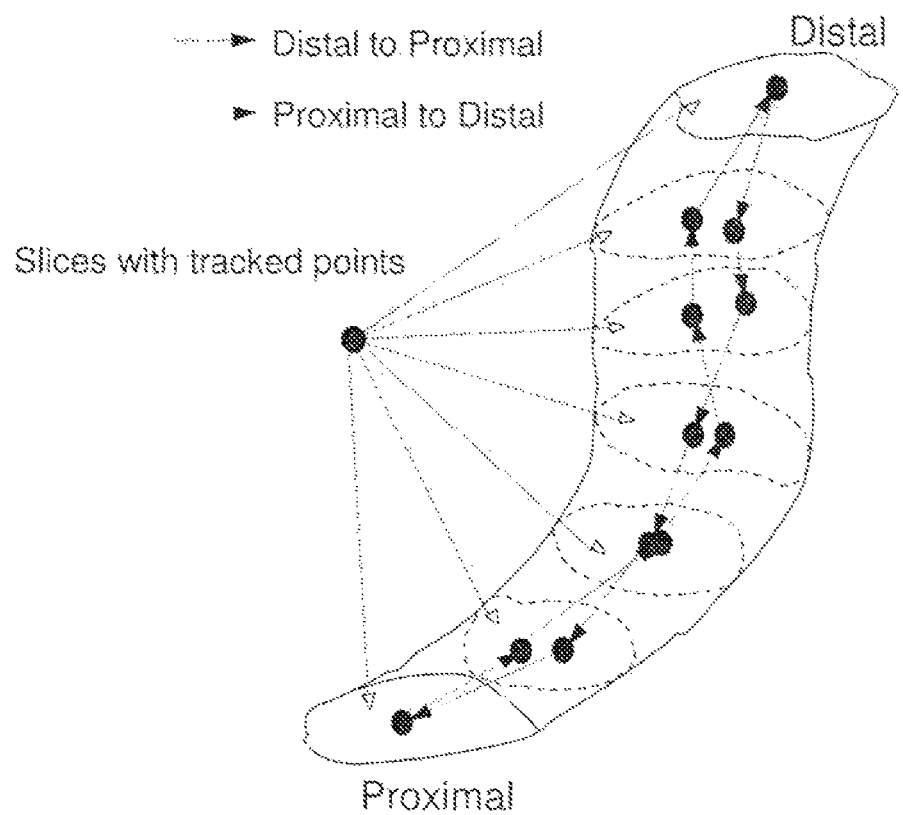
FIG. 7 illustrates bi-directional tracking.
Figure 8:
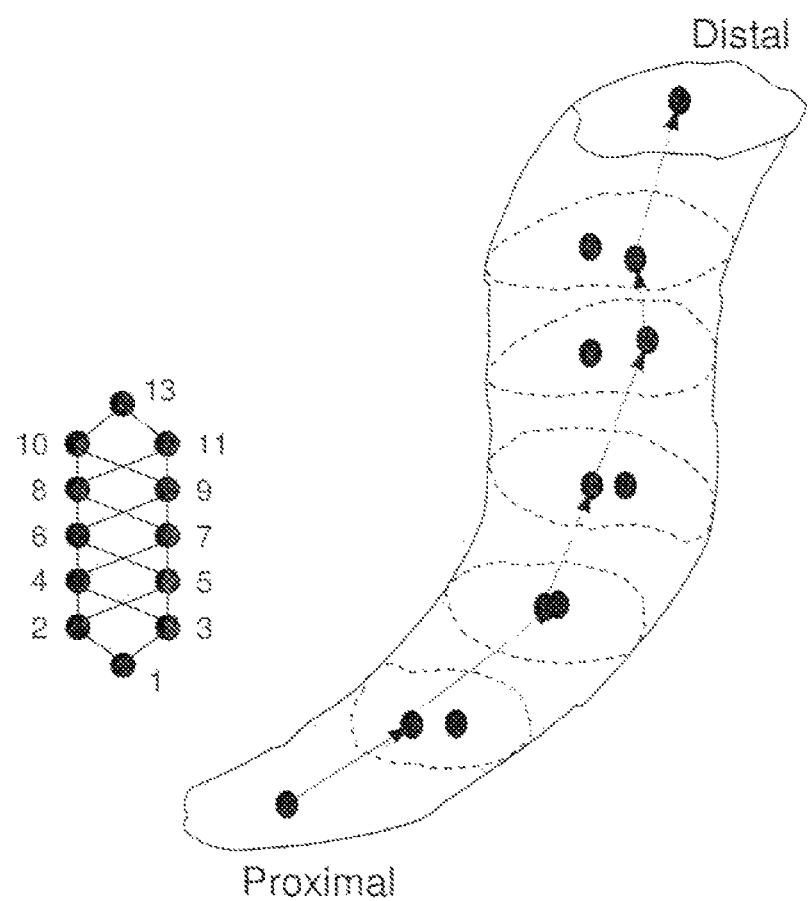
FIG. 8 illustrates path merging further to bi-directional tracking.

FIGS. 7 and 8 illustrate an alternative tracking and segmentation process. In a first stage of the process, two independent tracks may be computed: one from the proximal to distal image, and the other from the distal to the proximal image. The computation of tracked points in subsequent images may utilize a block-matching with mutual information (MI) process as a metric. MI is described more fully in E. W. Dijkstra, "A Note on Two Problems in Connexion with Graphs", Numerische Mathematik, v. 1, 1959, p. 269-271, incorporated herein by reference. As MI computation is computationally expensive, the number of grid points at which MI is computed may be restricted. It may so happen that the grid point at which the minimal MI is computed may have deviated significantly with respect to the final destination point. In order to control this movement, an added constraint may be applied that compares the angle between the initial, final and projected points to a particular threshold. The projected point may be selected if the angle made by these points is greater than the threshold, otherwise the tracked point from the previous image may be used as the new projected point.

In an optional second stage of the process, the tracked points may be validated with the seed optimization module to ensure that they lie in true luminal regions, while correcting for potential outliers. The final stage of the process builds a single contiguous path from the start to the end images. This is represented in FIG. 7.

The tracked points may be made nodes of an undirected graph. The nodes may be joined by arcs whereby a condition is applied that nodes from the same image should not be joined. The number of nodes may be restricted to a single circular template around each tracked point. To compute the arc-weights between nodes, MI or a sum of absolute difference between normalized CDF (cumulative distribution functions) between circular patches centered at each tracked points may be used. Furthermore, to penalize large deviations between tracked points, the arc-weights may be scaled by the Euclidean distance between the tracked points. Having formed the graph, the shortest spanning path between the start (e.g., Proximal) to the end (e.g., Distal) image may be determined using Dijkstra's algorithm. The result is a track map from the start to the end images, along with a mask indicating the approximate region in which the segmentation algorithm should be implemented, which is shown in FIG. 8.

Given the various alternatives provided above, tracked points obtained from the various alternatives can be applied concurrently and merged into a single path.

Figure 9:
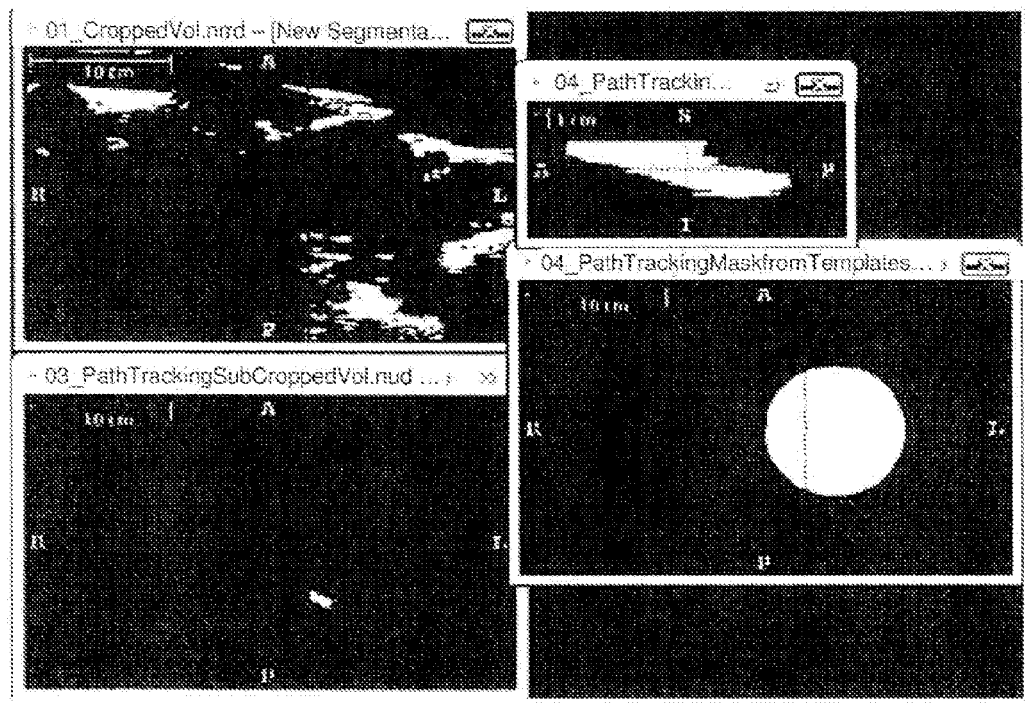
FIG. 9 is a graphical representation of the output from tracking.
Figure 10:
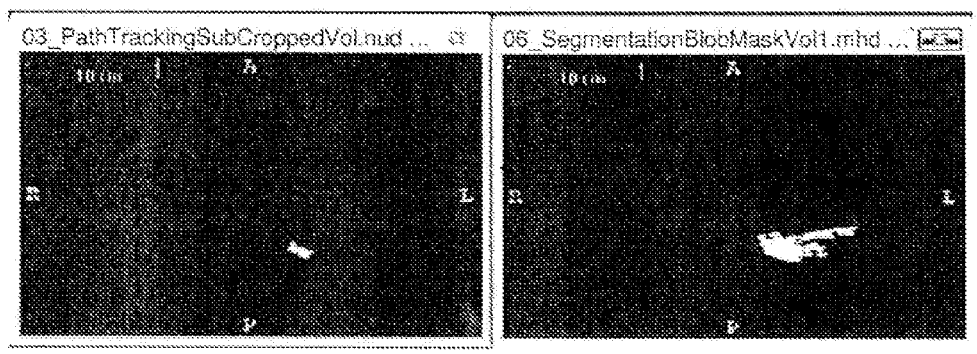
FIG. 10 is a graphical representation of clustering obtained from tracking.

The segmentation process further comprises isolation of a largest contiguous blob between the images corresponding to the user-defined regions of interest. The segmentation utility may apply a bottom-up clustering algorithm, for example statistical region merging (SRM), described more fully in R. Nock and F. Nielsen, "Statistical Region Merging", IEEE Trans. PAMI, v. 26, no. 11, November 2004, p. 1452-1458, incorporated herein by reference. In SRM, the only tunable parameter is a quality-factor, Q, that determines the success of the algorithm. Biologically, plaque is prone to occur in the ICA rather than the CCA. Thus, a lower Q-value may be selected for the CCA than the ICA. Some form of window-leveling (i.e., contrast adjustment) may further be applied on the volume prior to segmentation. The original SRM algorithm uses the mean pixel intensity as a predicate. However unlikely, this may sometimes lead small clusters that persist in the image volume. In order to remove such small regions, additional predicates like entropy, size, or convexity can be used to consolidate the blobs, as is described in F. Calderero and F. Marques, "Region Merging Techniques using Information Theory Statistical Measures", IEEE Trans. Image Processing, v. 19, no. 6, June 2010, p. 1567-1586; P. Felzenszwalb and D. Huttenlocher, "Efficient Graph-Based Image Segmentation", Int. J. Comp. Vision, v. 59, no. 2, September 2004; and P. L. Rosin, "Shape Partitioning by Convexity", IEEE Trans. Systems, Man and Cybernetics, Part A: Systems and Humans, v. 30, no. 2, February 2000, p. 202-210; each of which is incorporated by reference herein. The result of the segmentation result for the case shown in FIG. 8 may be seen in FIG. 9.

The blobs (or clusters) are expected to be contiguous provided the user selects images having similar pixel characteristics. The final task in the segmentation algorithm involves blob selection that gives us a contiguous binary mask across the span of images selected by the user.

Provided that the lumen is the blob having the smallest mean intensity across the image volume, and the lumen is present in all images, blob selection may be determined by selecting the ratio:

$$R_i = \frac{Avg_i}{Convexity_i}$$

$Avg_i$: Average grayscale intesity of blob $Convesity_i$: Ratio of volume to convex hull volume of blob and select the blob having the smallest value. For further accuracy, the computation may be restricted to those blobs that lie on seed points generated from the path map. Consequently, outlier blobs will be excluded from the selection criterion. Additionally, the presence of two contiguous, yet disjoint blobs, emanating from both start and end images may be determined to be in error.

Figure 11:
FIG. 11 is a graphical representation of a segmented output and visualization output for a first cine frame.
Figure 12:
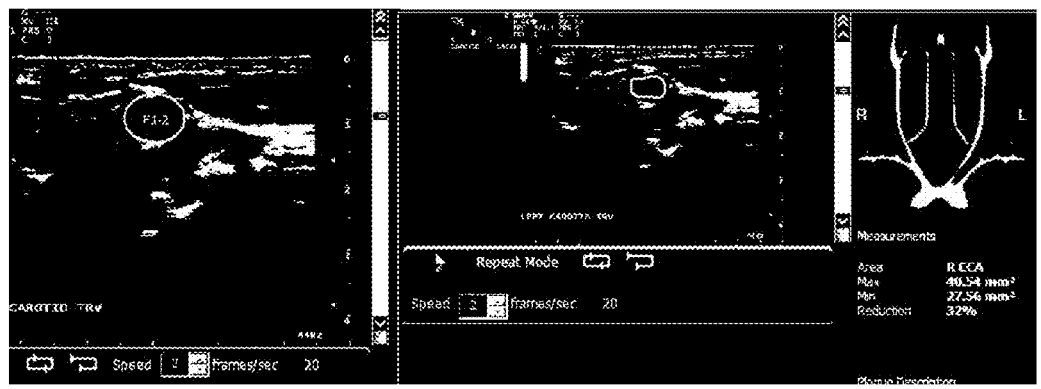
FIG. 12 is a graphical representation of a segmented output and visualization output for a last cine frame.

Referring now to FIGS. 11 and 12, the segmented output and visualization output for a first and last marked cine frame, respectively, are shown.

The visualization output utility is operable to generate a visualization to be output to the operator by an output device. In one aspect, the visualization output utility generates a graphical operator interface displaying one or more of the images and a 3D visualization generated from the images.

Figure 13:
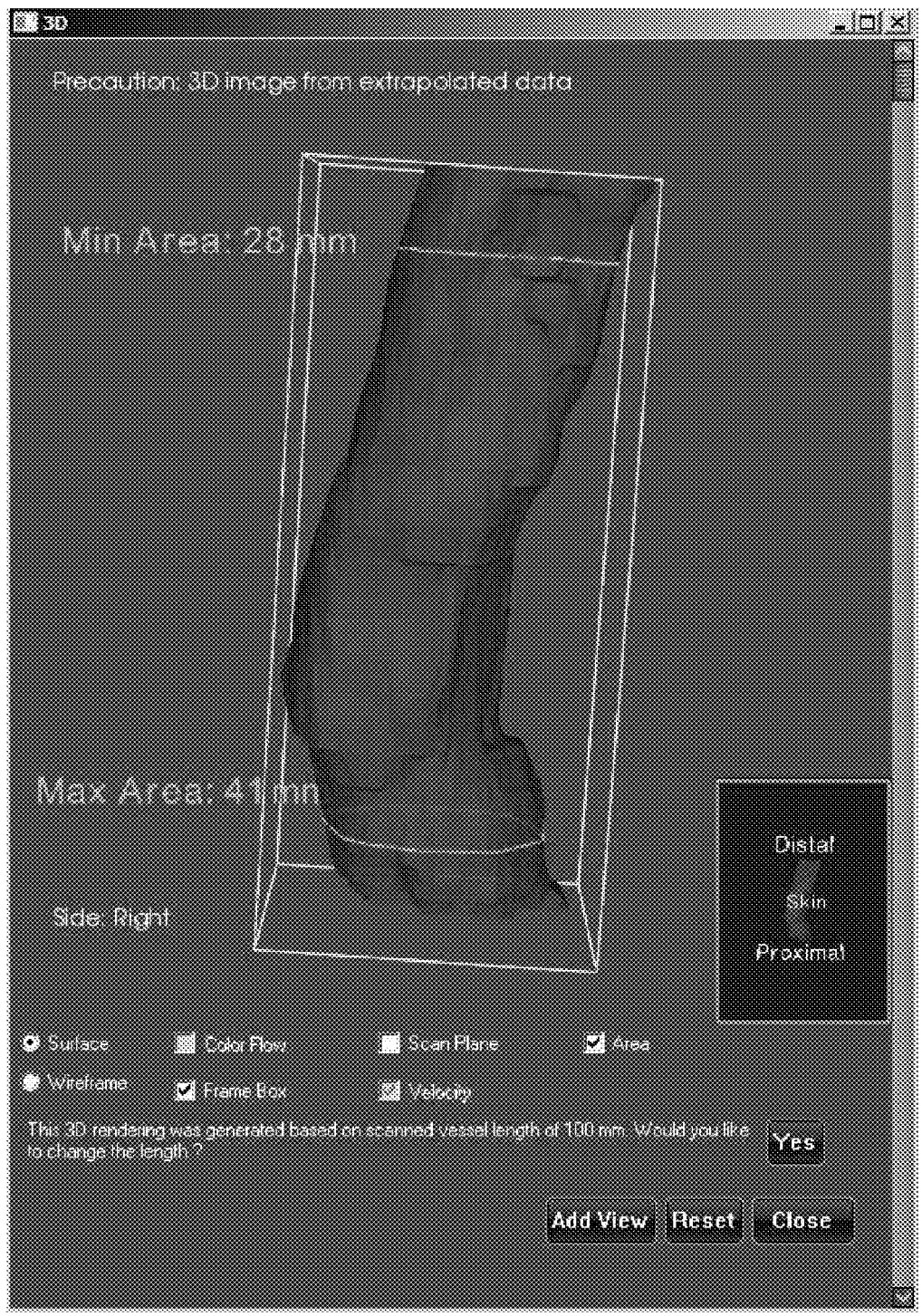
FIG. 13 is a graphical representation of a 3D visualization of a blood vessel.

Referring now to FIG. 13, the 3D visualization is generated from the lumen and outer wall that were previously determined. A third axis, being the length of the blood vessel for example, can be determined by the operator inputting the measurement that was taken from the patient.

The plaque accumulation can also be shown. Preferably, each of the lumen, outer wall and plaque accumulation can be displayed in different colors for ease of reference by the operator. The 3D visualization may also display other tissue and/or the adventitia and intima, as may have been obtained by the transverse segmentation utility.

The operator can interact with the 3D visualization, for example to zoom and rotate the visualization; to enable or disable the display of one or more of the objects, appearing in the visualization (e.g., one or more of the lumen, outer wall, plaque accumulation, etc.), or to change the colors of any of the objects.

Figure 14:
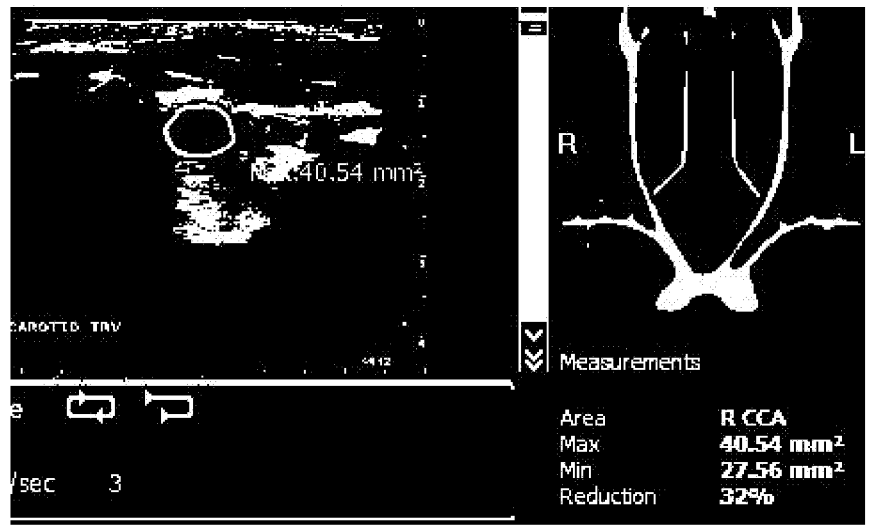
FIG. 14 is a graphical representation of a cine frame annotated with measurements.
Figure 15:
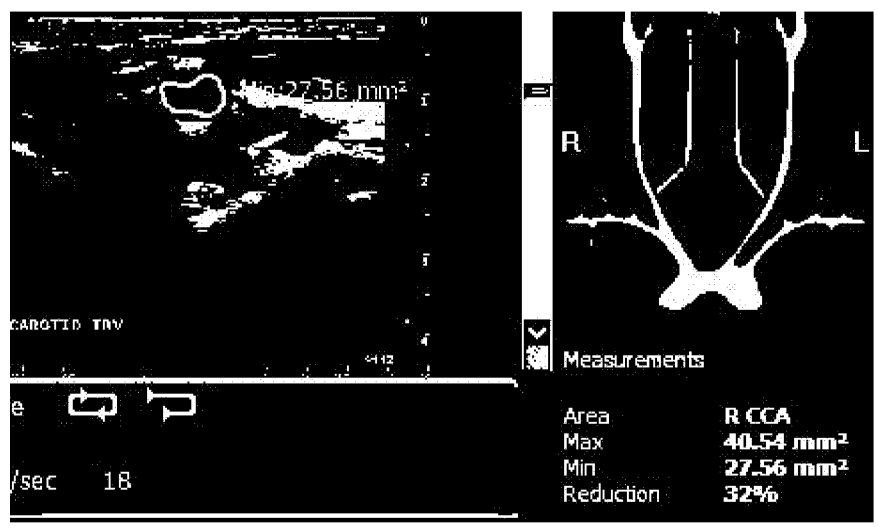
FIG. 15 is another graphical representation of a cine frame annotated with measurements.

Referring now to FIGS. 14 and 15, the visualization output utility is further operable to determine and display various measurements for the region of interest in any of the cine frames. The measurements may comprise the minimum and maximum points (i.e., diameters) in the region of interest; the increase or reduction in size of the region of interest across the shape of the plaque accumulation (or lesion) as the center of the axis rotates around the region of interest. The measurements may be annotated on the displayed image and/or visualization. Further measurements may be made manually be an operator and annotated by the operator on the displayed image and/or visualization using the input device. Further, the visualization output utility may enable the operator to enable or disable the display of any of the measurements.

Figure 16:
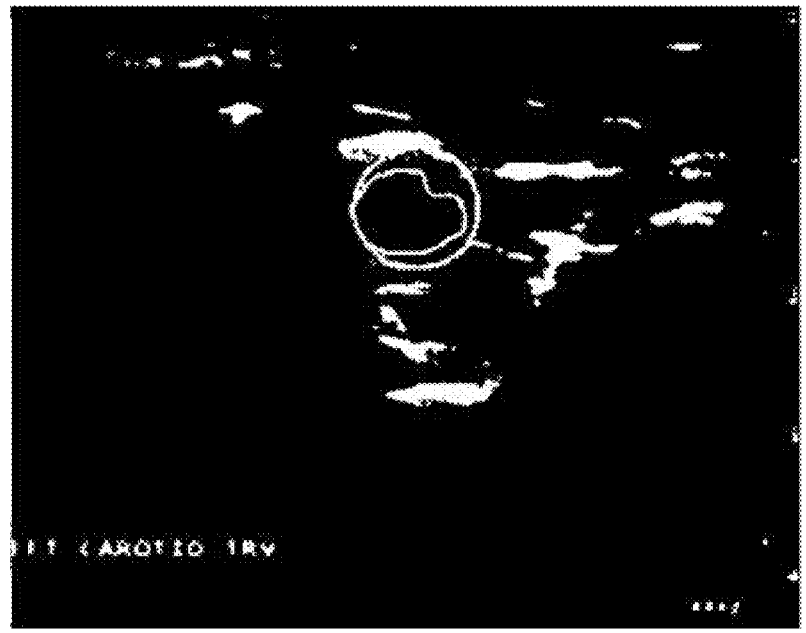
FIG. 16 is a graphical representation of a cine frame showing the lumen segmentation and outer wall output, which further displays to the operator the plaque accumulation.
Figure 17:
FIG. 17 is a graphical representation of another cine frame showing the lumen segmentation and outer wall output, which further displays to the operator the plaque accumulation.

Referring now to FIGS. 16 and 17, the visualization output utility may display one or more of the images showing the lumen segmentation and outer wall output, which further displays to the operator the plaque accumulation.

Figure 18:
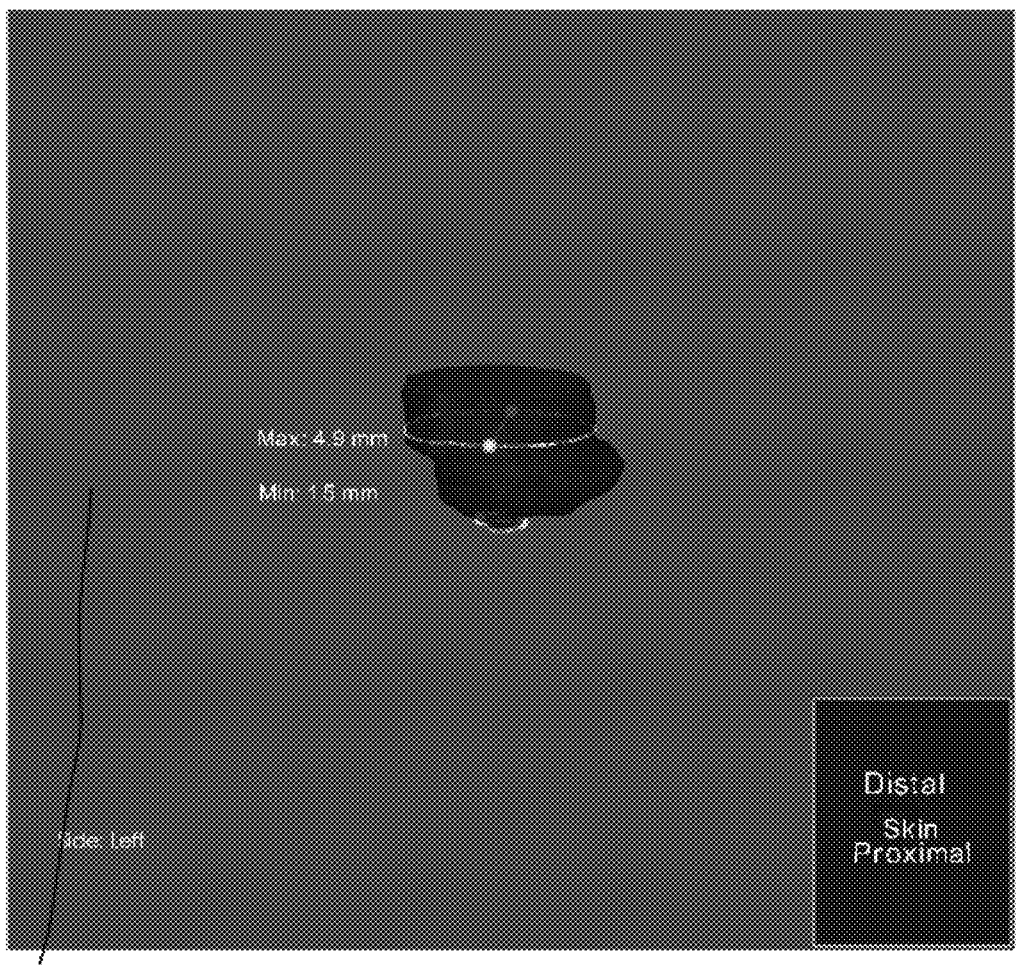
FIG. 18 is a graphical representation of an overlay of an orientation window to describe to the operator the location of the visualization relative to other landmarks.

Referring now to FIG. 18, the visualization output utility may overlay an orientation window to describe to the operator the location of the visualization relative to other landmarks, such as the distal ICA, skin and proximal CCA.

Figure 19:
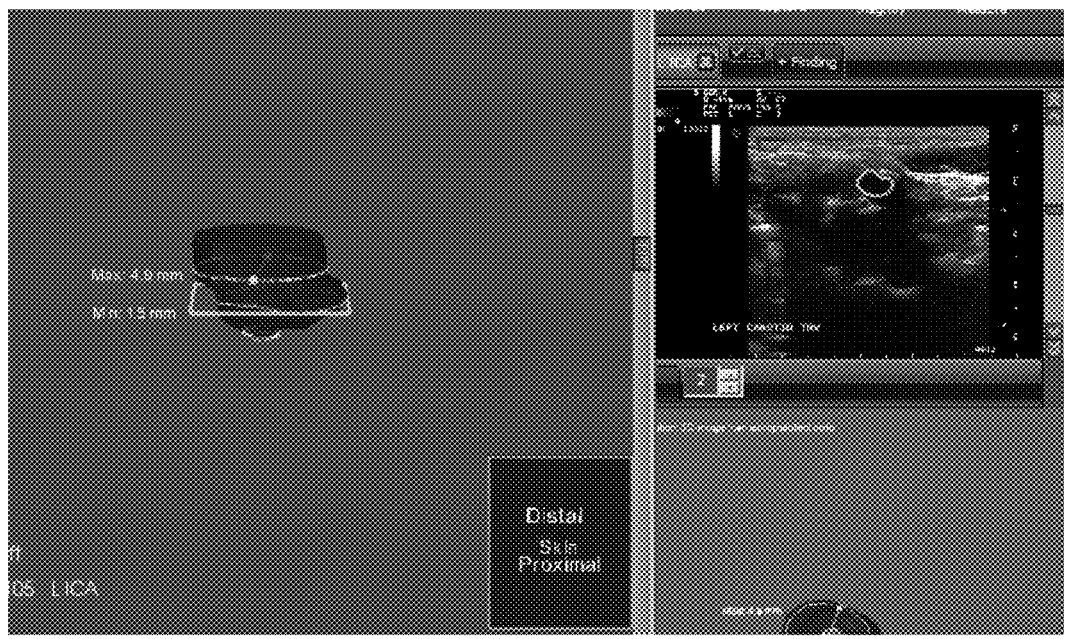
FIG. 19 is a graphical representation of a synchronization plane on the visualization that corresponds to a particular one of the images.

Referring now to FIG. 19, the visualization output utility may display a synchronization plane on the visualization that corresponds to a particular one of the images. The corresponding image may be shown simultaneously. As the operator manipulates the visualization, the corresponding image can be changed to reflect the location in the visualization that the operator is manipulating.

Figure 20:
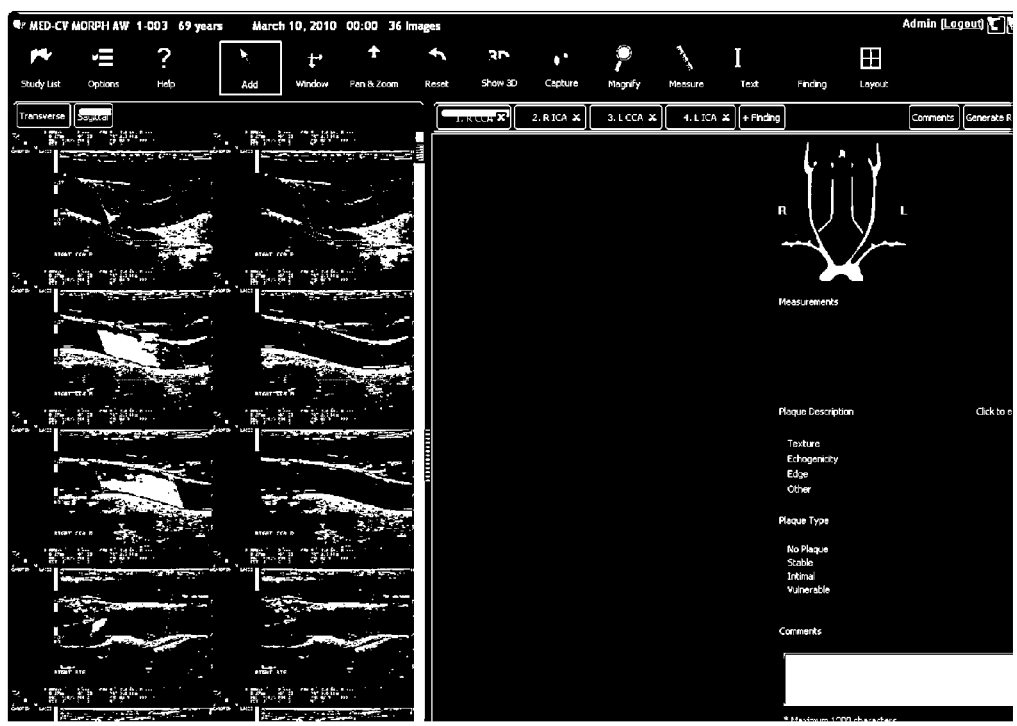
FIG. 20 is a graphical representation of a visualization providing additional information and measurements based on a sagittal scan.

Referring now to FIG. 20, the visualization output utility may further be operable to provide additional information and measurements based on the sagittal scan.

The sagittal segmentation utility may perform a semi-automatic image processing process that takes as input a matched pair of Doppler and B-mode sagittal images and a manually selected seed point inside the Doppler or the B-mode image domains. The sagittal segmentation utility provides an measurement of the distances inside the Doppler color image. The measurements are meant to speed up and improve the overall efficiency of the expert reader. The sagittal segmentation utility may apply a plurality of sub-processes, including color segmentation; determining the upper and lower color contours; generating the middle curve from upper and lower color contours; generate normals to the middle curve; measure normal distances; and report the minimum and maximum normal distances. The sagittal segmentation utility is operable to output to the visualization output utility the normal lines and global minimum and maximum distances. The visualization output utility may be operable to enable the operator to manually modify the spacing between the normal line with the final results being presented in the B-mode image domain.

The sagittal segmentation utility takes as input a matched pair of sagittal ultrasound images. The sagittal segmentation utility segments out the color Doppler image while the output is shown in the B-mode image domain. The Doppler color image is segmented using a color segmentation algorithm and the largest color blob may be selected as the representative blob for distance measurements. Wall segmentation may be based on detection of line like structures in an image using specialized filters.

The sagittal segmentation utility performs: (a) Doppler color blob segmentation that outputs the anterior/posterior lumen/wall coordinates and; (b) analysis to generate the normals to the central curve and compute the normal distances while reporting the global minimum/maximum values.

Segmentation takes as input a pair of matched Doppler and B-mode images and a seed point in the Doppler or B-mode image domain, and provides the top and bottom edges of the segmented Doppler blob and normal lines to the central curve (which is the average of the top and bottom edges) and the minimum and maximum global normal distances.

Doppler color blob segmentation may segment the largest blob in the Doppler color image. Due to the complexity of the shape of a blood vessel, segmentation may compute the convex hull and remove small size blobs that lie in a preconfigured area range. To further increase computation speed, the input image may be cropped using the computed segmented blob region of interest.

The edges of the largest Doppler blob are determined and the top and bottom edges are saved. The beginning and end coordinates of each edge may be computed using a preconfigured threshold value that removes a portion of the beginning and/or end of the edge from the size of the generated Doppler blob. For example, a preconfigured value of 10% may be used on both ends.

Curve analysis may consider the B-mode image. The smallest region of interest that encompasses the blob may be selected and cropped from the image to reduce computation time. The region of interest may be isolated and the outline thereof determined. A computation may be made of the central curve inside the color Doppler blob, being generated from the top and bottom edges. The normals to the central curve may also be generated by fitting a line to a small number of points from the central curve and generating normal lines to the interpolated central curve. Optionally, outliers that vary from the interpolated central curve by a preconfigured amount may be removed.

Morphological filters may also be applied to the color Doppler blob to remove small regions where flow direction is reversed. This allows the large blob to be considered as a plurality of small blobs for removal from the large blob.

The resulting top and bottom edges, central curve, and minimum and maximum global distances can be used to augment the measurements shown by the visualization output utility.

The graphical operator interface may further display a video clip comprising the plurality of frames.

The visualization output utility may store the visualization, including any corresponding measurements, to the memory, or to any remote location including a DICOM archive. Compression may be applied to any of the stored data. Compression may be a proprietary lossless RLE-based compression scheme, such as one derived from DICOM RLE compression, optimized to extract either color or gray images effectively.

The visualization output utility may further generate reports, including a depiction of the 3D visualization and any desired measurements. These reports may be output as a proprietary file or other file, such as PDF, DICOM secondary capture, DICOM PDF, or DICOM structured report.

Although the above has been described with reference to certain specific example embodiments, various modifications thereof will be apparent to those skilled in the art without departing from the scope of the claims appended hereto.

What is claimed is:

1. A method for generating a three dimensional visualization from a plurality of two dimensional images obtained by a transverse scan, the method comprising the steps of:
   generating a plurality of transverse scans of a target area with an image generation device;
   segmenting a region of interest in each image by:
      projecting a plurality of radial profiles at angularly equi-spaced radii from a lumen centroid to an edge of the lumen, wherein end points of the plurality of radial profiles form a closed contour;
      modeling the lumen using a multi-level thresholding algorithm to identify a plurality of pixels of the image which are within the region of interest;
      obtaining an ellipse to encapsulate the region of interest; and
      temporally smoothing the region of interest in each image;
   tracking an anatomical structure within the region of interest between each image; and
   rendering a three-dimensional visualization using said segmented and tracked region of interest.

2. The method of claim 1, wherein said transverse scan includes a cinema graphic moving picture.

3. The method of claim 1, wherein said region of interest is defined by a seed point defined in at least two of said images.

4. The method of claim 3, wherein said region of interest is further defined by an ellipse surrounding said seed point.

5. The method of claim 3, further comprising tracking said region of interest by said seed points.

6. The method of claim 1, further comprising stabilizing said region of interest.

7. The method of claim 1, wherein said tracking comprises generating two independent tracks.

8. The method of claim 7, wherein one of said independent tracks is generated from a first of said images to a second of said images and another of said independent tracks is generated from said second of said images to said first of said images.

9. The method of claim 7, wherein said generating comprises utilizing a block-matching with mutual information process.

10. The method of claim 9, wherein said block-matching with mutual information process further comprises a constraint based on the angle generated by two of said seed points in an adjacent set of two of said images.

11. The method of claim 1, wherein the multi-level thresholding algorithm further comprises generating a grid pattern surrounding a center point of the region of interest.

12. The method of claim 1, wherein the multi-level thresholding algorithm further comprises disambiguating closely-located features within the image by applying a connected-component filtering process.

13. The method of claim 1, wherein temporally smoothing the region of interest in each image further comprises weighting an outer wall of the lumen based on a size of a manually marked region of interest.

14. The method of claim 13, wherein weighting further comprises:
   filtering each image; and
   generating a histogram of a median filtered image.

15. The method of claim 13, further comprising the steps of:
   generating a plaque threshold value;
   generating a radial profile of the lumen centroid to the outer wall of the lumen for each image;
   filtering each image using a Kalman filtering process; and
   generating a plaque accumulation value based on a space between the lumen and the outer wall of the lumen.

16. The method of claim 1, wherein tracking the anatomical structure within the region of interest between each image further comprises using a cross-correlation process.

17. The method of claim 1, further comprising the steps of:
   automatically detecting at least one of a measurement of the region of interest, the at least one measurement comprising at least one of: a minimum diameter of the region of interest, a maximum diameter of the region of interest, and a cross-sectional area of the diameter of the region of interest; and
   calculating a percentage of the region of interest affected by an abnormality based on the at least one detected measurement of the region of interest.

18. The method of claim 1 wherein the lumen further comprises a blood vessel.

19. A method for generating a three dimensional visualization from a plurality of two dimensional images obtained by a transverse scan, the method comprising the steps of:
   generating a plurality of transverse scans of a target area with an image generation device;
   segmenting a region of interest in each image by:

projecting a plurality of profiles at the region of interest by identifying boundary points of the region of interest, wherein the boundary points form a closed contour about the region of interest;

modeling the region of interest by using a multi-level thresholding algorithm to identify a plurality of pixels of the image which are within the closed contour of the region of interest;

obtaining an ellipse to encapsulate the region of interest; and temporally smoothing the region of interest in each image;

tracking an anatomical structure within the region of interest between each image; and rendering a three-dimensional visualization using said segmented and tracked region of interest.

* * * * *